United States Patent
Garrec

(10) Patent No.: US 8,472,017 B2
(45) Date of Patent: Jun. 25, 2013

(54) KIT COMPRISING A SUPPORTING DEVICE FOR USE WITH A POLARIMETER

(75) Inventor: Ronan Garrec, Claix (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 434 days.

(21) Appl. No.: 12/813,130

(22) Filed: Jun. 10, 2010

(65) Prior Publication Data

US 2010/0315641 A1  Dec. 16, 2010

(30) Foreign Application Priority Data

Jun. 10, 2009  (EP) .................................. 09356040

(51) Int. Cl.
  *G01N 1/10* (2006.01)
  *G01J 4/00* (2006.01)
(52) U.S. Cl.
  USPC .......................................... 356/246; 356/367
(58) Field of Classification Search
  USPC ................................. 356/246, 367
  See application file for complete search history.

(56) References Cited

U.S. PATENT DOCUMENTS

| | | | |
|---|---|---|---|
| 3,443,423 A * | 5/1969 | Roberto ............................. 73/84 |
| 3,811,775 A * | 5/1974 | Abu-Saud ....................... 356/35 |
| 4,246,777 A | 1/1981 | Birner et al. |
| 5,003,174 A * | 3/1991 | Datwyler et al. ............. 250/343 |
| 5,307,680 A | 5/1994 | Drescher-Krasicka |
| 5,379,648 A | 1/1995 | Tiffin |
| 5,717,144 A | 2/1998 | Dunaway |
| 5,949,536 A * | 9/1999 | Mark ............................. 356/246 |
| 6,914,732 B1 * | 7/2005 | Wang et al. .................... 359/811 |
| 7,017,427 B1 | 3/2006 | Vacek |
| 2007/0119260 A1 | 5/2007 | Cox |

FOREIGN PATENT DOCUMENTS

| | | |
|---|---|---|
| FR | 2700613 | 1/1993 |
| FR | 2700613 | 7/1994 |
| GB | 2100432 | 12/1982 |
| WO | WO 2008/022942 | 2/2008 |
| WO | WO 2008/022942 A2 | 2/2008 |
| WO | WO 2008/022942 A3 | 2/2008 |

OTHER PUBLICATIONS

International Search Report and Written Opinion dated Jul. 16, 2010.
Extended European Search Report dated Nov. 4, 2009.

* cited by examiner

*Primary Examiner* — Roy M Punnoose
(74) *Attorney, Agent, or Firm* — Cozen O'Connor

(57) ABSTRACT

A kit having a supporting device for maintaining a transparent article having a longitudinal axis A, a proximal end and a distal end. The supporting device including a proximal holder including a port intended to receive the proximal end of the article, and a distal holder including a receiving part intended to receive the distal end of the article, the port and the receiving part being aligned on the same longitudinal axis B. The supporting device further having a compressor for putting the article under longitudinal compression directed towards a center of the article, when the article is mounted on the supporting device with its longitudinal axis A aligned on the longitudinal axis B, and a polarimeter. The invention also pertains to a method for measuring the stress inside an article made of transparent material.

18 Claims, 3 Drawing Sheets

KIT COMPRISING A SUPPORTING DEVICE FOR USE WITH A POLARIMETER

BACKGROUND OF THE INVENTION

1. Field of the Invention

The present invention relates to a kit comprising a supporting device for maintaining under compression in a substantially determined position an article made of a transparent material, and a polarimeter for measuring the stress in the material of the article once said article is mounted on said supporting device. The article may be a medical device like syringe bodies or ampoules. The invention further relates to a method for putting under compression an article made of a transparent material, such as syringe bodies and/or cartridges and/or ampoules and/or vials, using such a supporting device and a polarimeter, in order for example to perform further analysis of said article.

2. Description of the Related Art

A lot of medical devices are made of transparent material such as glass, polycarbonate, polyolefin like polyethylene, polypropylene, CCP (Cristal Clear polymer) or polystyrene. For such uses as those of the medical field, these medical devices must be totally safe and must not break when handled. Moreover, the medical devices made in brittle material such as glass or polycarbonate usually show complex shapes such as tubular shapes:

this is the case in particular of syringe bodies, cartridges, ampoules or vials used for storing and/or administering medicine to a patient.

Nevertheless, although it is known to measure the stress in a classical planar piece of transparent material such as flat glass for example, there still lacks a reproducible method for putting under compression an article and measuring the amount of stress inside such an article made of such a transparent material, in particular when the article has a complex shape.

Indeed, such a method and means for completing such a method in a reproducible way would be of great interest. Actually, it happens that a percentage of the just manufactured syringe bodies and/or ampoules which are provided to the pharmaceutical companies in order to be filled with the adequate medicine may break at the time they are handled.

SUMMARY OF THE INVENTION

There is therefore a need for a reproducible method for maintaining in compression, and optionally further measuring the resistance of, medical articles made of brittle transparent material such as glass, polyolefin or polycarbonate, and showing relatively complex shapes, such as tubular shapes.

The present invention aims at providing means, and in particular a kit comprising a specific supporting device, able to maintain, preferably under compression, and rotate the article to be measured, for completing such a reproducible method.

A first aspect of the present invention is a kit comprising a supporting device for maintaining under longitudinal compression an article made of transparent material and having a longitudinal axis A, a proximal end and a distal end, said supporting device including a proximal holder including a port intended to receive the proximal end of said article, and a distal holder including a receiving part intended to receive the distal end of said article, said port and said receiving part being aligned on the same longitudinal axis B, wherein said supporting device further comprises compression means for putting said article under longitudinal compression directed towards a center of said article, when said article is mounted on said supporting device with its longitudinal axis A aligned on said longitudinal axis B, said kit further including a polarimeter for measuring the stress in the material of the article when said article is mounted on said supporting device.

As will appear from the description below, "under longitudinal compression" means in the present application that, once the article is mounted on the supporting device of the kit of the invention, it is submitted to a minimum compressive force, exerted along the longitudinal axis A of said article and in the direction of the center of said article, so that said article does not detach or fall off from said supporting device under the effect of gravity, regardless of the direction of said longitudinal axis A and B, which are aligned on each other, with respect to the environing space: in other words, once the article is mounted on said supporting device, the article is submitted to said longitudinal compression regardless of the fact that the longitudinal axis B is vertical (supporting device in a vertical position), horizontal (supporting device in a horizontal position) or inclined (supporting device in any inclined position). In other words, the longitudinal compressive force applied to said article corresponds to a force above 0 Newton. As it will also appear from the description, this longitudinal compressive force may vary in a range from above 0 to less than 1000 Newton depending on which measurements need to be performed on said article. For example, the longitudinal compressive force is the force applied at least one end, for example at both ends, of the article, in the direction of the center of the article along its longitudinal axis, once the article is mounted on the supporting device.

In the present application, the distal end of an article is to be understood as meaning the end furthest from the user's hand and the proximal end is to be understood as meaning the end closest to the user's hand when the article is in use. Likewise, in this application, the "distal direction" is to be understood as meaning the direction of injection, and the "proximal direction" is to be understood as meaning the opposite direction to the direction of injection. By similarity, although the supporting device of the kit of the invention is not intended to be used for an injection operation, the term "proximal" applied to the supporting device of the kit of the invention, is used in reference to the part of the supporting device receiving the proximal end of said article, and the term "distal" applied to the supporting device of the kit of the invention, is used in reference to the part of the supporting device receiving the distal end of said article.

Thanks to the supporting device of the kit of the invention, and as will appear from the description below, the medical article, and in particular the tubular barrel of a syringe body or of a cartridge or of an ampoule or of a vial, is maintained under longitudinal compression in a determined position, for example horizontal, vertical or inclined, by means of its proximal and distal ends only contacting said supporting device. As a result, the space surrounding the article to be measured, and in particular the space surrounding the part of the article to be measured, is totally free of any disturbing element in the three directions. For example, the part of the article to be measured need not be in contact with or bear on an additional support, which would be likely to distort potential measures to be made on said article. In addition, in such determined position, the article or the tubular barrel may be rotated, again by means of its proximal and distal ends only contacting said supporting device. For example, if measurements are to be performed on the article with a polarimeter, there is no need of any additional supporting element that would interfere with the light sent by the polarimeter in the direction of the central part of the article or the tubular barrel. In particular, thanks to the structure and arrangement of the supporting device of the kit of the invention, the space between the proximal holder and the distal holder is free from any additional element. As a consequence, it is possible to use a polarimeter, and to focus the light of said polarimeter on the article or on the part of the article to be measured without any intermediate element located between the polarimeter and the article or such part of the article to be measured. The light of the polarimeter encounters therefore no obstacle before reaching the part of the article to be measured, for example the tubular barrel of a syringe body.

In an embodiment of the invention, at least one of said port and receiving part is rotatable around said longitudinal axis B.

In such an embodiment, because at least the port or the receiving part of the supporting device of the kit of the invention is rotatable, the article to be measured, once mounted on the supporting device of the kit of the invention, may be rotated. In case a polarimeter is used, this allows measuring the value of stress inside the article, for example inside the tubular barrel, or inside the distal tip, of a syringe body, after several rotations of the article or of the tubular barrel or of the distal tip to be measured. In case the article to be measured has a complex shape such as a tubular shape, for example a tubular barrel, this allows obtaining measures at different points of the circumference of the article or of the barrel, all along said circumference, and therefore to eventually obtain reproducible average values of the stress inside the article or barrel.

In an embodiment of the invention, said port and said receiving part are both rotatable around said longitudinal axis B. Such an embodiment allows a safer and smoother rotation of the article to be measured. The rotation may be completed manually by the user, or automatically by means of a motor.

In an embodiment of the invention, said port is fixed in translation with respect to said proximal holder along the direction of said longitudinal axis B. For example, when said port is also rotatable, such an embodiment allows to provide said proximal holder with a motor so as to render the rotation of said port automatic: an automatic rotation allows a quicker, safer, more repeatable and more reproducible rotation. In an embodiment of the invention, said port being rotatable, said proximal holder is further provided with a motor so as to render said rotation of said port automatic.

In an embodiment of the invention, said receiving part is movable in translation with respect to said distal holder along the direction of said longitudinal axis B. Such an embodiment allows adjusting the length of the space located between the port and the receiving part, so that articles of various lengths may be mounted on the supporting device. Such an embodiment also allows adjusting the longitudinal compressive force to be applied on the article once said article is mounted on said supporting device, by increasing or decreasing the distance between the port and the receiving part.

In an embodiment of the invention, the compression means comprises biasing means tending to urge one of said port and said receiving part toward the other one of said port and receiving part: for example, said distal holder is provided with biasing means tending to urge said receiving part in the proximal direction. Said biasing means may for example be under the form of a helical spring located around a longitudinal shaft bearing either the port or the receiving part. The presence of such a biasing means tending for example to urge the receiving part in the proximal direction allows the receiving part to abut on the distal end of the article to be measured, and contributes to set up the longitudinal compressive force enabling the safe maintaining of the article in the determined position. Such a longitudinal compressive force should nevertheless preferably not be greater than 1000 N so as to avoid that the article breaks once mounted on the supporting device. For example, in order to warrant that said longitudinal compressive force does not interfere with the optical vision at the time of measuring the stress inside the article with a polarimeter, said longitudinal compressive force is preferably less than 20 N.

In an embodiment of the invention, said port is provided with a distal conic part distally tapered. As it will appear later in the description, such an embodiment allows the port to be engaged, in particular with friction due to the presence of the longitudinal compressive force, inside the proximal end of the tubular barrel of a syringe body, for example at the level of the flange in the case the syringe body is provided with a proximal flange. Because the port is engaged with friction inside the proximal end of the article to be measured, the rotation of the port will cause the rotation of the article to be measured, such as the syringe body for example.

In another embodiment of the invention, said port is provided with a ring, the distal face of which is provided with a central recess. Such an embodiment may be used in particular with an ampoule, a cartridge or a vial having a proximal end provided with a flat bottom. In such a case, when the ampoule, cartridge or vial is mounted on the supporting device of the kit of the invention, the flat bottom of the ampoule, cartridge or vial is engaged in the central recess provided in the distal face of the ring, preferably by friction, in particular due to the presence of the longitudinal compressive force. As seen above for the previous embodiment, because the flat bottom of the proximal end of the ampoule, cartridge or vial is engaged with friction inside the central recess of the distal face of the ring of the port, the rotation of the port will cause the rotation of the article, ie the ampoule, the cartridge or the vial for example, to be measured.

In an embodiment of the invention, said receiving part is provided with a ring traversed by a central channel aligned on said longitudinal axis B. Such an embodiment allows the distal tip of a syringe body or an ampoule for example to be received safely within the receiving part. In particular, it is possible to mount a syringe body provided with a needle on the distal tip, the needle being received within said central channel.

For example, the proximal portion of said central channel has the shape of a cone distally tapered. Such a shape is particularly useful when the article to be measured, such as a syringe body or an ampoule, has a distal conic tip.

In alternative embodiments, the receiving part is adapted for receiving the distal end of a vial, such as a collar for example. In such a case, the receiving part may be provided with a ring, the proximal face of which is provided with a central recess intended to receive said collar.

In alternative embodiments, the receiving part is fixed in translation with respect to the distal holder and said distal holder is provided with a motor so as to render the rotation of said receiving part automatic. In other embodiments also, the port may be movable in translation with respect to the proximal holder, so as to adjust the length of the space defined between the port and the receiving part to the length of the article to be measured, and/or so as to adjust the value of the compressive force to be applied on said article. Also, the port may be urged towards the distal direction by means of a biasing means, in the same manner as described above for the receiving part.

In embodiments of the present invention, the kit further comprises said article made of a transparent material and having a longitudinal axis A, a proximal end and a distal end.

By "transparent material" is meant according to the present application, a material allowing at least 5% of light transmission in the visible, preferably allowing at least 50% of light transmission in the visible, and more preferably allowing at least 90% of light transmission in the visible. As an example, glass usually allows at least 90% of light transmission in the visible. For example, opalescent materials, which allow at least 5% of light transmission in the visible, for example at least 50% of light transmission in the visible, may be used in the present invention. Translucent materials, which allow the diffusion of a certain percentage of the light they receive, and which also allow at least 5% of light transmission in the visible, for example at least 50% of light transmission in the visible, may also be used in the present invention. Opalescent materials and translucent materials are therefore comprised in the term "transparent" according to the present application.

In an embodiment of the kit of the invention, said article has a substantially tubular shape, such as a syringe body, a cartridge, a vial or an ampoule.

For example, said transparent material is selected from glass, polyolefin, polycarbonate and combinations thereof. In embodiments, the transparent material is glass.

In an embodiment of the kit of the invention, said article is a syringe body having a tubular barrel provided with a substantially conic distal tip, said supporting device comprising a port provided with a distal conic part distally tapered and a receiving part provided with a ring traversed by a central channel aligned on said longitudinal axis B, said distal conic part being engaged by friction in a proximal end of said tubular barrel and said conic distal tip being engaged in said central channel when said syringe body is mounted on said supporting device. In particular, in such an embodiment, when said syringe body is mounted on said supporting device, said syringe body is maintained under longitudinal compression.

In an embodiment of the invention, said syringe body is made of glass.

In an embodiment of the invention, said article being mounted on said supporting device, and said transparent material having a refractive index RI, said kit is immersed within a liquid having a refractive index substantially identical to RI. Such an embodiment allows measuring the stress within the thickness of the transparent material forming the article with a polarimeter: for instance, in the case of a syringe body having a barrel out of glass, such an embodiment allows to measure the stress within the thickness of the barrel wall, using a polarimeter.

The kit of the invention further includes a polarimeter for measuring the stress inside the article, once said article is mounted on said supporting device.

Alternatively or in combination, the kit of the invention may further include other analysis instruments, like for example microscopes or cameras used in combination with a light source such as UV, visible or LASER light, for measuring other parameters and/or properties of the article. As examples of such instruments, one can cite instruments for analyzing the quality of the homogeneity of the material forming the article along a circumference of said article for example or along the length of the article, or the quality of printings performed on the outer or inner surface of the article, etc. . . . In embodiments, the articles to be measured may be provided with an inner coating and/or an outer coating. In such cases, the kit of the invention may also include analysis instruments for measuring properties, like thickness, homogeneity, etc., of said coating(s).

Another aspect of the invention is a method for measuring the stress inside an article having a longitudinal axis A, a proximal end and a distal end and made of a transparent material, comprising the steps of i) mounting said article on a supporting device as described above, by engaging said proximal end of said article into said port and said distal end of said article into said receiving part, ii) applying on said article a longitudinal compressive force of more than 0 Newton and iii) measuring the stress inside the article with a polarimeter by directing the light of said polarimeter towards said article.

In embodiments, the longitudinal compressive force ranges from above 0 to less than 1000 N. In embodiments, the compressive force ranges from 20 to 1000 N. The longitudinal compressive force may range from 300 to 1000 N.

For example, the method of the invention may be used for first stressing the material forming the article and then measuring the stress inside the article in order to test such material in such a stressing condition. In such embodiments, the longitudinal compressive force may range from 20 to 1000 N, preferably from 300 to 1000 N.

In other embodiments, for example when one wishes to measure the stress inside the article when said article is not submitted to specific stressing conditions, the longitudinal compressive force may range from above 0 to 20 N.

For example, the longitudinal compressive force may be adjusted by increasing or decreasing the distance between the port and the receiving part of the supporting device of the invention. Alternatively or in combination, the longitudinal compressive force may be adjusted by selecting a specific constant K for the helical spring of the supporting device of the kit of the invention as described above.

Preferably, said article has a substantially tubular shape, such as a barrel. Preferably, said article is as described above. Said article may be chosen among cartridges, syringe bodies, ampoules and vials as described on FIGS. 2a to 2d and may be made of transparent material such as glass, polyolefin or polycarbonate.

In an embodiment of the method of the invention, said article having a substantially tubular shape, such as a barrel, said article is rotated around the longitudinal axis B of an angle selected in the range of 0-360° and the stress inside the article is measured.

Generally, the window of analysis is adapted to the rotation angle. The smaller the window is, the smaller the angle of analysis is, the higher the number of measurements is, and then, the more precise the resulting measurement is.

For example, the article is rotated 6 times of an angle of 30° and the stress inside the article is measured after each rotation. A repeatable, reproducible average value of the stress present inside the article, the barrel in the case of a syringe body, can therefore be obtained.

Such a method, thanks to the kit of the invention, allows obtaining reproducible measures of the stress inside the article made of the transparent material, the barrel in the case of a syringe body. In embodiments, the article being a syringe body comprising a barrel and a distal tip, the stress may be measured inside the barrel and/or inside the distal tip.

It is therefore possible to set up a limit value above which the measured article should not be kept for future operations and should be disposed of, because too likely to break when handled.

BRIEF DESCRIPTION OF THE DRAWINGS

The kit and method of the invention will now be further described in reference to the following description and attached drawings in which.

DETAILED DESCRIPTION OF THE PRESENTLY PREFERRED EMBODIMENTS

Figure 1:
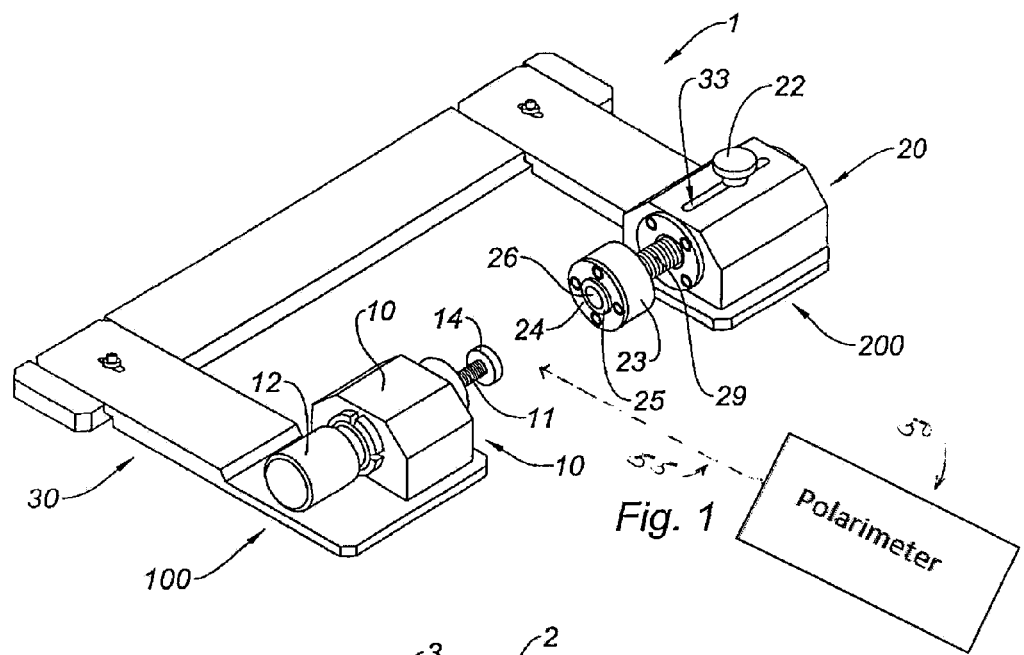
FIG. 1 is a perspective view of the supporting device of the kit of the invention.
Figure 2A:
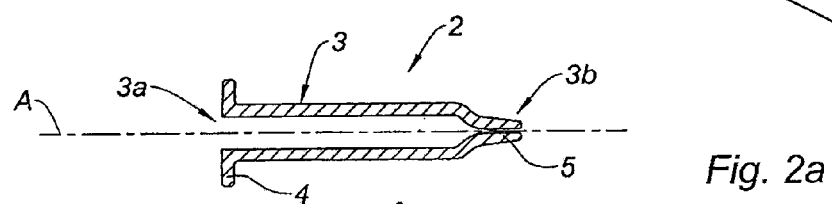
FIG. 2a is a cross section view of a syringe body that can be assessed with the measuring method of the invention.
Figure 2B:
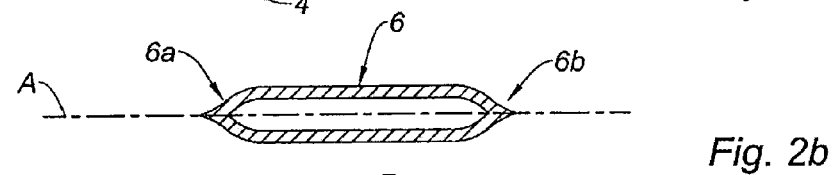
FIG. 2b is a cross section view of first embodiment of an ampoule that can be assessed according to the method of the invention.
Figure 2C:
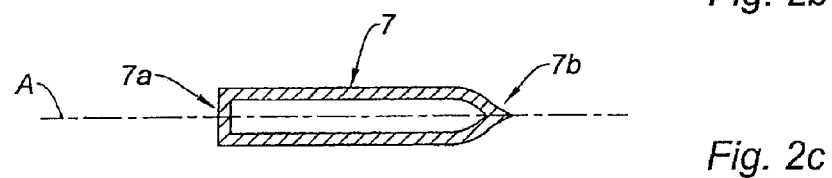
FIG. 2c is a cross section view of a second embodiment of an ampoule that can be assessed according to the method of the invention.
Figure 2D:
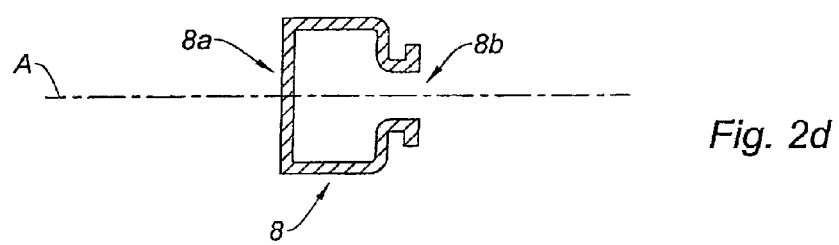
FIG. 2d is a cross section view of a vial that can be assessed according to the method of the invention.
Figure 3:
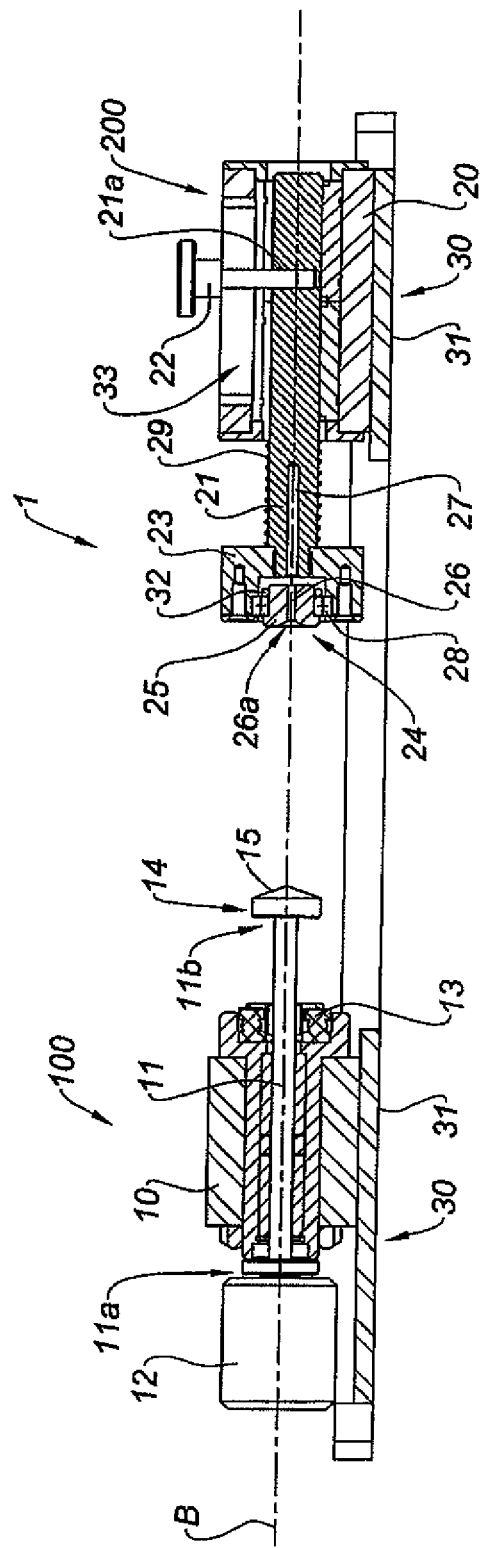
FIG. 3 is a cross section view of the supporting device of FIG. 1 along a plane containing the longitudinal axis B.

With reference to FIGS. 1 and 3 is shown a supporting device 1 of a kit according to the invention, capable of maintaining under longitudinal compression and rotating an article having a longitudinal axis A, such as those shown on FIGS. 2a to 2d.

On FIG. 2a, is shown an article having a substantially tubular shape under the form of a syringe body 2 comprising a tubular barrel 3 having a longitudinal axis A, a proximal end 3a and a distal end 3b. The proximal end 3a of the barrel 3 is provided with an outer flange 4 providing bearing surfaces for the user at the time of injection. The distal end 3b of the barrel 3 is provided with a conic distal tip 5 providing a passage for the transfer of a medicine contained in the barrel 3 from the syringe 2 to the site of injection. The conic distal tip 5 is intended to receive a needle (not shown).

The syringe body 2, as well as the barrel 3, of FIG. 2a are preferably made out of a transparent material, such as glass, polyolefin or polycarbonate. Glass and polycarbonate are brittle material which may break.

By "transparent material" is meant according to the present application, a material allowing at least 5% of light transmission in the visible, preferably allowing at least 50% of light transmission in the visible, and more preferably allowing at least 90% of light transmission in the visible. Opalescent and translucent materials are comprised in the term "transparent" as used in the present application.

On FIG. 2b is shown another embodiment of an article suitable for the supporting device 1 of the kit of the invention. The article of FIG. 2b has a longitudinal axis A and has a substantially tubular shape under the form of an ampoule 6 intended to contain a product (not shown) to be administered. Although the two opposite ends of such an ampoule 6 are identical, for purposes of the present application, it is hereinafter referred to a proximal end of the ampoule 6, under the form of a proximal tapered tip 6a, and to a distal end of said ampoule 6, under the form of a distal tapered tip 6b, as shown on FIG. 2b.

The ampoule 6 of FIG. 2b may be made out of transparent brittle material such as glass, polyolefin or polycarbonate.

On FIG. 2c is shown another embodiment of an article suitable for the supporting device 1 of the kit of the invention. The article of FIG. 2c has a longitudinal axis A and has a substantially tubular shape under the form of an ampoule 7. The ampoule 7 has a proximal end under the form of flat bottom 7a, and a distal end under the form of a distal tapered tip 7b.

The ampoule 7 of FIG. 2c may be made out of transparent brittle material such as glass, polyolefin or polycarbonate.

On FIG. 2d is shown another embodiment of an article suitable for the supporting device 1 of the kit of the invention. The article of FIG. 2d has a longitudinal axis A and has a substantially tubular shape under the form of a vial 8. The vial 8 has a proximal end under the form of flat bottom 8a, and a distal end under the form of a collar 8b.

The vial 8 of FIG. 2d may be made out of transparent brittle material such as glass, polyolefin or polycarbonate.

Alternatively, the article suitable for the present invention may be a cartridge.

With reference to FIGS. 1 and 3, the embodiment of the supporting device 1 of the kit of the invention shown is particularly suitable for receiving a syringe body 2 such as described at FIG. 2a. The supporting device 1 includes a proximal holder 100, intended to receive the proximal end 3a of the barrel 3 of the syringe body 2 of FIG. 2a, and a distal holder 200, intended to receive the distal end 3b of the barrel 3 of the syringe body 2 of FIG. 2a.

On the example shown the proximal holder 100 comprises a solid body 10 traversed by a shaft 11 extending along the longitudinal axis B of said solid body 10. At its proximal end 11a, the shaft 11 is provided with a handle 12 allowing the shaft 11 to be rotated manually around the longitudinal axis B. In an alternative embodiment not shown, the solid body 10 is provided with a motor allowing the automatic rotation of the shaft 11. In order to facilitate and to better control the rotation of the shaft 11, the solid body 10 may include ball bearings 13 located between the solid body 10 and the shaft 11, as shown on FIG. 3.

The shaft 11 is further provided at its distal end 11b with a port 14 extending beyond said solid body 10 in the distal direction. The port 14 is provided with a distal conic part 15 distally tapered, the function of which will be explained later.

On the example shown, the shaft 11 and therefore the port 14 are fixed in translation with respect to the solid body 10 along the direction of said longitudinal axis B.

On the example shown on FIGS. 1 and 3, the distal holder 200 also comprises a solid body 20 traversed by a shaft 21 extending along the longitudinal axis B of said solid body 20 of said distal holder 200. The shaft 21 of the distal holder 200 is movable in translation with respect to said solid body 20 along the direction of said longitudinal axis B, in the distal or in the proximal direction. In order to block the shaft 21 in translation with respect to said solid body 20 in a determined position corresponding for example to the size of the article to be mounted on the supporting device, said shaft 21 is provided with a traversing hole 21a perpendicular to its longitudinal axis: the traversing hole 21a receives a screw 22 able to slide within a longitudinal recess 33 arranged in said solid body 20 as said shaft 21 is moved in the distal or proximal direction: when the shaft 21 has reached the adequate determined position, the screw 22 is tightened so as to come in abutment on the solid body 20, thereby blocking said shaft 21 in said determined position. The shaft 21 may be advanced in the distal direction or withdrawn in the proximal direction in order to adjust to the length of the article to be mounted on the supporting device of the kit of the invention, and then blocked in translation as just described.

In an embodiment not shown, the shaft is not provided with a traversing hole, and the screw is directly tightened on said shaft 21 so as to block it in translation.

On the embodiment shown on FIGS. 1 and 3, the shaft 21 of the distal holder 200 is provided at its proximal end with a head 23 lodging a receiving part 24 intended to receive the conic distal tip 5 of the syringe body 2 of FIG. 2a. The receiving part 24 is provided with a ring 25 traversed by a central channel 26 aligned on said longitudinal axis B. The proximal portion 26a of the central channel 26 has the shape of a cone distally tapered, the function of which will be explained later.

As shown on FIG. 3, the central channel 26 of the head 23 may be prolonged by a central hole 27 extending within the shaft 21 on a certain length.

Moreover, ball bearings 28 are provided between the head 23 and the receiving part 24 allowing the receiving part 24 to rotate with respect to the head 23.

An annular seal 32 is mounted around the ring 25 for securing said ring 25 to the head 23. Biasing means, under the form of a helical spring 29 located around the shaft 21, are provided, between the solid body 20 and the head 23. Whatever the relative position of the shaft 21 with respect to the solid body 20, the helical 29 spring is in a stressed state, so as to urge the head 23, and therefore the receiving part 24, in a proximal direction. The inner force of the helical spring 29 contributes to setting up the desired longitudinal compressive force to be applied to the article to be mounted on the supporting device 1. For instance, a specific constant K of the helical spring 29 may be selected in order to obtain the desired longitudinal compressive force in function of the size of the article to be mounted on the supporting device 1. As a result, the helical spring 29 forms part of compression means for putting the article under longitudinal compression directed towards the center of the article, when the article is mounted on the supporting device with its longitudinal axis A aligned on the longitudinal axis B.

On the embodiment shown on FIGS. 1 and 3, the supporting device 1 of the kit of the invention is further provided with a sole 30 having an even bottom face 31 intended to be put on a horizontal plane. Both proximal and distal holders (100, 200) of the supporting device 1 of the kit of the invention are permanently fixed to said sole 30 so that their position with respect to each other may not vary.

As will appear from description of FIG. 4 below, the article to be measured by the supporting device 1 of FIGS. 1 and 3 is maintained under longitudinal compression in a substantially horizontal position once installed on said supporting device 1. As seen above, the longitudinal compressive force applied to the article, once said article is mounted on the supporting device is above 0 Newton, so that said article does not fall off or detach from the supporting device. Depending on the purposes for which the article is mounted on the supporting device 1, the longitudinal compressive force may vary from above 0 to 1000 N.

For instance, as will appear below, the user may wish to measure with a polarimeter 50 the properties of the material forming the article when said material is submitted to a specific stress: in such a case, the longitudinal compressive force may vary from 20 N to 1000 N. or even from 300 N to 1000 N.

In other embodiments, the user may wish to measure the stress inside the article, with a polarimeter 50, under conditions as close to the regular use of said article as possible. In such a case, the longitudinal compressive force may vary from above 0 to 20 N in order not to interfere with the measures of the stress inside the article with the polarimeter 50.

In an embodiment not shown, the proximal and distal holders (100, 200) may be in a fixed position with respect to each other, so that the article to be measured is maintained in a vertical position or in an inclined position, in other words, so that the longitudinal axis B is vertical or inclined.

Figure 4:
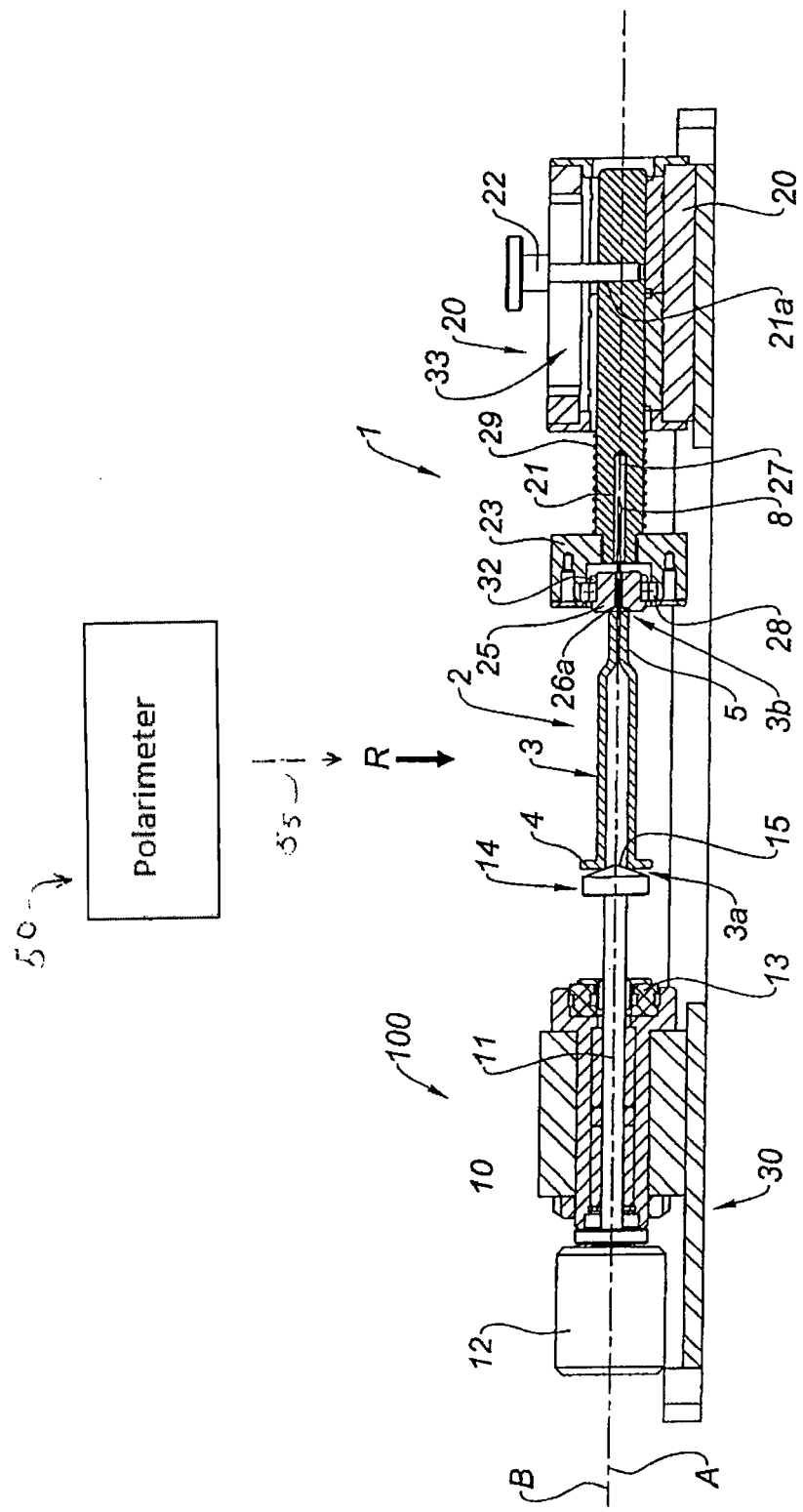
FIG. 4 is a cross section view of the supporting device of FIG. 3 once the syringe body of FIG. 2a is mounted on said supporting device.

With reference to FIG. 4, the supporting device 1 of FIGS. 1 and 3 is shown with the syringe body 2 of FIG. 2a mounted thereon. The references designating the same elements as in FIGS. 1, 2a and 3 have been maintained. The syringe body 2 of FIG. 2a is further provided with a needle 8 fixed at the conic distal tip 5 of the barrel 3.

As appears on FIG. 4, the proximal end 3a of the barrel 3 of the syringe body 2 is engaged on the distal conic part 15 of the port 14, and the distal end 3b of the barrel 3 of the syringe body 2, in other words the conic distal tip 5, is engaged in the proximal portion 26a of the central channel 26 of the head 23. As appears from the figure, the shape of the distal conic part 15 of the port 14 is adapted to receive syringes having open proximal ends with a wide range of diameters. The needle 8 is received within the central hole 27 of the shaft 21, aligned on the central channel 26. Moreover, the helical spring 29 being in a stressed state, it contributes to the longitudinal compressive force applied on the syringe body 2 along its longitudinal axis A and in the direction of the center of said syringe body, thereby allowing the proximal end 3a and the distal end 3b to be engaged respectively with said port 14 and said receiving part 24 with friction. This longitudinal compressive force, while being above 0 Newton, is nevertheless preferably less than 1000 N, and more preferably less than 20 N in order not to interfere with the measures of the stress inside the article with a polarimeter 50 as described below.

As a consequence, when the shaft 11 of the proximal holder 10 is rotated around the longitudinal axis B, for example manually by a user operating the handle 12, the syringe body 2 and the barrel 3 are caused to also rotate around the longitudinal axis B.

Moreover, as appears clearly on FIG. 4, the structure and arrangement of the supporting device 1 of the kit of the invention allows the syringe body 2, and in particular the barrel 3, to be maintained in a determined position, and to be rotated in said position, by means of its proximal and distal ends (3a, 3b) only being in contact with the supporting device 1. Thanks to the supporting device 1 of the kit of the invention, there is no need of any intermediate part or element having to be operated in the vicinity of the tubular barrel 3. As a consequence, when the article, for example the syringe body 2, is analyzed with a polarimeter 50, the light 55 coming from the polarimeter 50, for example along the direction materialized by the arrow R on FIG. 4 or from any other direction around the article or syringe body 2, does not encounter undesired obstacle before reaching the barrel 3. This allows obtaining reliable measures of the stress present inside the barrel 3. Actually, the light 55 sent by the polarimeter 50 goes through a first wall of the barrel 3 and through the diametrically opposed wall of said barrel 3. The polarimeter 50 therefore measures the addition of the stress present inside the two walls of the barrel 3 traversed by the light 55: it measures the stress present inside the barrel 3.

In an embodiment not shown, the syringe body 2 of FIG. 4 is replaced by one of the ampoule (6; 7) of FIGS. 2b and 2c. In such embodiments, the port of the supporting device of the kit of the invention is provided with a ring, the distal face of which is provided with a central recess. When the ampoule 6 of FIG. 2b is to be mounted on the supporting device of the kit of the invention, the central recess is similar to the central channel of the receiving part 24 of FIGS. 1 and 3 in order to receive the conic proximal end 6a of the ampoule 6. Alternatively, when the ampoule 7 of FIG. 2c is to be mounted on the supporting device of the kit of the invention, the central recess of the ring of the port has inner dimensions adapted to receive the flat bottom 7a of the proximal end 7a of the ampoule 7.

In an embodiment not shown, the vial 8 of FIG. 2d is mounted on the supporting device of the kit of the invention: in such a case, each of the port and the receiving part comprises a ring provided with a central recess intended to receive the flat bottom 8a, respectively the collar 8b.

Alternatively, a cartridge may be mounted and put under longitudinal compression on the supporting device of the kit of the invention, so as to be further assessed.

The method of the invention for putting under compression, measuring the stress inside, and optionally further assessing the quality and/or the strength of, an article having a longitudinal axis A, a proximal end and a distal end, said article being made of a transparent material such as glass, polyolefin or polycarbonate can therefore be implemented as follows: the article to be measured is mounted on the supporting device 1 as described above for FIG. 4, ie by engaging said proximal end of said article into said port and said distal end of said article into said receiving part, and applying on said article a longitudinal compressive force of more than 0 Newton. The value of the longitudinal compressive force may be adjusted as described above. In case a measure of the stress inside the article under no specific stressing conditions is to be performed, the longitudinal compressive force is generally less than 20 N and a polarimeter 50 is used. Alternatively, in case a measure of the stress inside the article under specific stressing conditions is to be performed, the longitudinal compressive force ranges generally from 20 N to 1000 N, or even from 300 N to 1000 N and a polarimeter is used. A first measure may be completed using the polarimeter 50, the light 55 of which is directed towards the part of the article to be assessed, in particular towards the tubular barrel 3 in case of a syringe body 2 as described in FIG. 2a. Alternatively or in combination, the stress inside the distal tip may also be measured.

Any known polarimeter is suitable for the method of the invention. As an example, one can cite the polarimeter "STRAMO" from the company SGCC.

For example, the following steps may be completed: After a first measure is completed, the article, the syringe body 2 of FIG. 4, is rotated for example by an angle of 30°. A second measure is completed. This step is repeated 5 times. The method of the invention allows performing a series of at least six measures for example, all around the circumference of the barrel 3 of the syringe 2, thereby enabling to obtain reliable average values. The method of the invention is therefore reproducible and can be used in an industrial process in order to determine whether the syringe bodies of a batch just manufactured are likely to break in the future or not.

For example, it is possible to determine a maximum limit value of stress above which it is decided that the risk that the syringe body breaks when subsequently handled for example during a fill in operation is too high, therefore justifying that said syringe body be disposed of. It is then possible to implement the method of the invention at an industrial process level in order to maintain only the syringe bodies satisfying to a stress value, measured according to the method of the invention, below said maximum limit value.

In an embodiment of the invention not shown, the supporting device 1 and the syringe body 2 mounted thereon as shown on FIG. 4 are immersed within a liquid having a refractive index substantially identical to that of the transparent material forming the barrel 3, for example glass. Such an embodiment allows measuring the stress within the thickness of the wall of the barrel, with a polarimeter, and not only inside the barrel 3, as explained above.

The kit and the method of the invention therefore allow improving the manufacturing process of articles made of a brittle transparent material such as syringe bodies and ampoules in the medical field.

I claim:

1. A kit comprising a supporting device for maintaining under longitudinal compression an article made of a transparent material having a longitudinal axis A, a proximal end and a distal end, said supporting device comprising:
    a proximal holder having a port intended to receive the proximal end of said article, and
    a distal holder having a receiving part intended to receive the distal end of said article; said port and said receiving part being aligned on a common longitudinal axis B; said supporting device further comprising compression means for putting said article under longitudinal compression directed towards a center of said article, when said article is mounted on said supporting device with its longitudinal axis A aligned on said longitudinal axis B, said kit further comprising a polarimeter for measuring the stress in the material of the article when said article is mounted on said supporting device, wherein the port includes one of:
    a distal end shaped to engage an inner surface of the proximal end of the article, and
    a recess having an inner surface shaped to engage the proximal end of the article.

2. The kit according to claim 1, wherein at least one of said port and receiving part is rotatable around said longitudinal axis B.

3. The kit according to claim 1, wherein said port is fixed in translation with respect to said proximal holder along the direction of said longitudinal axis B.

4. The kit according to claim 1, wherein said receiving part is movable in translation with respect to said distal holder along the direction of said longitudinal axis B.

5. The kit according to claim 1, wherein said compression means comprises biasing means tending to urge one of said port and said receiving part toward the other one of said port and receiving part.

6. The kit according to claim 1, wherein said port is provided with a distal conic part distally tapered.

7. The kit according to claim 1, wherein said receiving part is provided with a ring traversed by a central channel aligned on said longitudinal axis B.

8. The kit according to claim 1, further comprising said article.

9. The kit according to claim 8, wherein said article has a substantially tubular shape.

10. The kit according to claim 9, wherein said article is one of a syringe body, a cartridge, a vial, and an ampoule.

11. The kit according to claim 8, wherein said transparent material is selected from one or more of glass, polyolefin, and polycarbonate.

12. The kit according to claim 8, wherein said transparent material is glass.

13. The kit according to claim 8, wherein said article is a syringe body having a tubular barrel provided with a substantially conic distal tip, said supporting device comprises a port provided with a distal conic part distally tapered and a receiving part provided with a ring traversed by a central channel aligned on said longitudinal axis B, said distal conic part being engaged by friction in a proximal end of said tubular barrel and said conic distal tip being engaged in said central channel when said syringe body is mounted on said supporting device.

14. The kit according to claim 8, wherein said article is mounted on said supporting device, and said transparent material has a refraction index RI, and wherein said supporting device and article are immersed within a liquid having a refraction index substantially identical to RI.

15. A method for measuring stress inside an article having a longitudinal axis A, a proximal end and a distal end and made of a transparent material, the method comprising the steps of: i) mounting said article on a supporting device according to claim 1 by engaging said proximal end of said article into said port and said distal end of said article into said receiving part, ii) applying on said article a longitudinal compressive force of more than 0 Newton, and iii) measuring the stress inside the article with a polarimeter by directing the light of said polarimeter towards said article.

16. The method according to claim 15, wherein said longitudinal compressive force ranges from above 0 to 1000 N.

17. The method according to claim 15, wherein said longitudinal compressive force ranges from above 0 to 20 N.

18. The method according to claim 15, wherein said article has a substantially tubular shape, said article is rotated around the longitudinal axis B of an angle selected in the range of 0-360° and in that the stress inside the article is measured.

* * * * *